United States Patent [19]

Rutsch et al.

[11] Patent Number: 4,837,350
[45] Date of Patent: Jun. 6, 1989

[54] PROCESS FOR THE PREPARATION OF BENZOIN SULFONATES

[75] Inventors: Werner Rutsch, Fribourg; Rinaldo Hüsler, Marly, both of Switzerland

[73] Assignee: Ciba-Geigy Corporation, Ardsley, N.Y.

[21] Appl. No.: 129,574

[22] Filed: Dec. 7, 1987

[30] Foreign Application Priority Data

Dec. 15, 1986 [CH] Switzerland .......................... 4988/86

[51] Int. Cl.$^4$ ............................................. C07C 143/68
[52] U.S. Cl. ....................................... 558/52; 549/473; 549/73; 549/72; 549/70; 546/284; 546/283; 546/262; 546/190; 546/187; 544/152; 544/146; 544/130
[58] Field of Search ..................... 558/52; 549/473, 73, 549/72, 70; 546/284, 283, 262, 190, 187; 544/152, 146, 130

[56] References Cited

U.S. PATENT DOCUMENTS

| | | | |
|---|---|---|---|
| 3,732,273 | 5/1973 | Heine et al. | 558/52 |
| 4,347,248 | 8/1982 | Wright, Jr. et al. | 540/473 |
| 4,510,290 | 4/1985 | Kirchmayr et al. | 525/162 |
| 4,699,949 | 10/1987 | Berner et al. | 525/162 |

OTHER PUBLICATIONS

I. J. Borowitz, J. Org. Chem., 34 (1969), 1595–1600.

Primary Examiner—Nicky Chan
Attorney, Agent, or Firm—Harry Falber; Stephen V. O'Brien

[57] ABSTRACT

Benzoin esters of aromatic sulfonic acids can be obtained in high yield from benzoin and the respective sulfonyl halide in molar amounts of a base by carrying out the reaction at low temperature in an organic solvent with the addition of water. Aqueous NaOh or KOH can be used as base in this process.

9 Claims, No Drawings

PROCESS FOR THE PREPARATION OF BENZOIN SULFONATES

The present invention relates to a process for the preparation of benzoin esters of aromatic sulfonic acids, especially of crystalline benzoin sulfonates.

Such benzoin sulfonates are disclosed in European patent applications EP-A-No. 84 515 and EP-A-No. 132 225, and are proposed therein as latent curing catalysts for acid-curable resins which can be thermally or photolytically activated. It is important for this utility that the esters do not contain sulfonic acid. They can also be used as starting materials for the preparation of 4,5-diphenylthiazolines and 4,5-diphenyloxazolines which are intermediates for the synthesis of certain cyanine dyes.

Sulfonic acid esters are customarily prepared from the appropriate alcohols and sulfonyl chlorides in the presence of an HCl acceptor. This general process has also been used for the preparation of sulfonates of benzoin and derivatives thereof.

Thus in Ber. 60, 664 (1927), Z. Földi describes the reaction of benzoin with benzenesulfonyl chloride in benzene with the addition of solid NaOH. The crude sulfonate is obtained in 36% yield after the benzene phase has been washed with water and concentrated by evaporation.

The reaction of benzoin with methansulfonyl chloride in benzene and in the presence of 2 equivalents of triethylamine is described by I. J. Borowitz et al. in J. Org. Chem. 34, 1599 (1969). After separation of the amine salt, the benzene phase is washed with water and concentrated by evaporation. The benzoin mesylate is obtained in 69% yield after recrystallisation from ethyl acetate. The analogous reaction of benzoin in benzene with toluenesulfonyl chloride and 2 equivalents of triethylamine proceeds very slowly if carried out at room temperature. About 50% of benzoin is still present after 20 hours. If the reaction is speeded up by heating, then secondary reactions occur and the by-products obtained include benzil. All in all, the known prior art processes for the preparation of benzoin esters of aromatic sulfonic acids are therefore unsatisfactory.

As the sulfochlorides employed as well as the sulfonic acid esters obtained are sensitive to hydrolysis, it is generally preferred to carry out the reaction of sulfochlorides with benzoins under anhydrous conditions. Surprisingly, it has now been found that, under specific conditions, the reaction can also be carried out in the presence of water and that, under said conditions, the presence of water accelerates the reaction and leads to an increase in yield. The conditions are that, during the reaction, there is never a substantial excess of base present and that the reaction is carried out at fairly low temperature. The reaction is carried out in an inert solvent.

Accordingly, the present invention relates to a process for the preparation of sulfonic acid esters of formula I

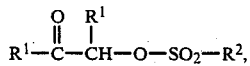  (I)

wherein
R$^1$ is phenyl or phenyl which is substituted by halogen, C$_1$-C$_4$alkyl, C$_1$-C$_4$alkoxy, C$_1$-C$_4$alkylthio, —NH—CO—(C$_1$-C$_4$alkyl), —NH—CO—phenyl, morpholino, piperidino or a radical —N(R$^3$)(R$^4$), or is naphthyl or tetrahydronaphthyl, each unsubstituted or substituted by halogen or C$_1$-C$_6$alkyl, or is a univalent 5- or 6-membered heteroaromatic radical which contains O, S or N and is unsubstituted or substituted by halogen or C$_1$-C$_4$alkyl, R$^2$ is phenyl or phenyl which is substituted by halogen, C$_1$-C$_{20}$alkyl, C$_1$-C$_4$haloalkyl, C$_1$-C$_4$alkoxy, C$_1$-C$_4$alkylthio, nitro, —NH—CO—(C$_1$-C$_4$alkyl), —NH—CO—phenyl or benzoyl, or is naphthyl or naphthyl which is substituted by halogen or C$_1$-C$_{20}$ alkyl, or is a univalent 5- or 6-membered heteroaromatic radical which contains O, S or N and is unsubstituted or substituted by halogen or C$_1$-C$_6$alkyl, and R$^3$ and R$^4$ are each independently of the other C$_1$-C$_4$alkyl, allyl or cyclohexyl, by reaction of a benzoin compound of formula II

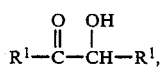  (II)

with a sulfonyl halide of formula III

  (III)

wherein X is fluorine, chlorine or bromine, in an inert organic solvent and in the presence of a base, which process comprises carrying out the reaction in the presence of water, using 1 to 1.5 equivalents of base per mole of sulfonyl halide of formula III, and carrying out the reaction at a temperature below 40° C.

R$^1$ in formulae I and II is an unsubstituted or substituted carbocyclic or heterocyclic aromatic radical and may be phenyl, fluorophenyl, chlorophenyl, bromophenyl, dichlorophenyl, tolyl, xylyl, ethylphenyl, isopropylphenyl, tert-butylphenyl, methoxyphenyl, ethoxyphenyl, butoxyphenyl, dimethoxyphenyl, methylthiophenyl, butylthiophenyl, acetylaminophenyl, propionylaminophenyl, benzoylaminophenyl, dimethylaminophenyl, dibutylaminophenyl, methylcyclohexylaminophenyl, naphthyl, chloronaphthyl, bromonaphthyl, methylnaphthyl, isopropylnaphthyl, hexylnaphthyl, tetrahydronaphthyl, ethyltetrahydronaphthyl, furyl, thienyl, pyridyl or methylpyridyl.

R$^1$ is preferably phenyl or phenyl which is substituted by halogen, C$_1$-C$_4$alkyl, C$_1$-C$_4$alkoxy or C$_1$-C$_4$alkylthio, or naphthyl, furyl, pyridyl or thienyl, each unsubstituted or substituted by C$_1$-C$_6$alkyl, and is most preferably phenyl, chlorophenyl or tolyl.

R$^2$ in formulae I and II is an unsubstituted or substituted carbocyclic or heterocyclic aromatic radical and may be phenyl, chlorophenyl, bromophenyl, chloromethylphenyl, trifluoromethylphenyl, tolyl, xylyl, tert-butylphenyl, hexylphenyl, octylphenyl, nonylphenyl, dodecylphenyl, trimethylphenyl, hexadecylphenyl, octadecylphenyl, methoxyphenyl, ethoxyphenyl, butoxyphenyl, methylthiophenyl, ethylthiophenyl, tert-butylthiophenyl, nitrophenyl, acetylaminophenyl, butyrylaminophenyl, benzoylaminophenyl, benzoylphenyl, naphthyl, chloronaphthyl, bromonaphthyl, methylnaphthyl, butylnaphthyl, hexylnaphthyl, octylnaphthyl, nonylnaphthyl, decylnaphthyl, dodecylnaphthyl, octadecylnaphthyl, eicosylnaphthyl, furyl, thienyl or pyridyl.

$R^2$ is preferably phenyl, naphthyl or pyridyl, each unsubstituted or substituted by halogen, $C_1$-$C_4$alkyl, halomethyl, $C_1$-$C_4$alkoxy, nitro or —NH—CO—($C_1$-$C_4$alkyl), and is most preferably phenyl, bromophenyl, chlorophenyl, tolyl or naphthyl.

The preferred sulfonyl halide is a sulfonyl chloride of formula III, wherein X is chlorine.

Representative examples of sulfonic acid esters which can be prepared by the process of this invention are:
2-[(tolylsulfonyl)oxy]-1,2-diphenylethan-1-one,
2-[(phenylsulfonyl)oxy]-1,2-diphenylethan-1-one,
2-[($\beta$-naphthylsulfonyl)oxy]-1,2-diphenylethan-1-one,
2-[(m-nitrophenylsulfonyl)oxy]-1,2-diphenylethan-1-one,
2-[(2,4,6-trimethylphenylsulfonyl)oxy]-1,2-diphenylethan-1-one,
2-[(p-bromophenylsulfonyl)oxy]-1,2-diphenylethan-1-one,
2-[(tolylsulfonyl)oxy]-1,2-bis-(o-chlorophenyl)ethan-1-one,
2-[(tolylsulfonyl)oxy]-1,2-bis-(p-methylphenyl)ethan-1-one.

The reaction of the compound of formula II with that of formula III is effected in approximately equimolar proportion, but a small excess of sulfonyl halide can be used. The preferred molar ratio of II:III is 1:1 to 1:1.3.

A hydroxide, oxide or alcoholate of an alkali metal or alkaline earth metal may be suitably used as base. It is preferred to use a water-soluble base, most preferably aqueous NaOH or KOH. The base is added to the reaction mixture such that a substantial excess of base is never present. It is preferred to use 1 to 1.2 equivalents of base per mole of sulfonyl halide of formula III.

A polar or non-polar solvent may be used as solvent. Polar solvents are usually miscible with water, so that a monophase reaction takes place. Non-polar solvents are usually water-immiscible, so that two liquid phases can form in the course of the reaction.

At all events the solvents must be inert to sulfonyl halides, i.e. they may not contain for example any nucleophilic OH or NH groups. Examples of useful solvents are: benzene, toluene, xylene, chlorobenzene, nitrobenzene, dichlorobenzene, methylene chloride, tetrachloroethane, dibutyl ether, methyl ethyl ketone, methyl isobutyl ketone, acetone, tetrahydrofuran, dioxane, acetonitrile, dimethylformamide, dimethylacetamide or N-methylpyrrolidone. It is preferred to use methyl ethyl ketone, toluene, xylene, methylene chloride, chlorobenzene, dichlorobenzene, dibutyl ether, methyl isobutyl ketone, acetone, dioxane, tetrahydrofuran or dimethylformamide.

Particularly suitable solvents are those of average polarity which are able to take up a certain amount of water, e.g. methyl ethyl ketone, acetone or tetrahydrofuran.

The reaction can be speeded up by the catalysts which are known for the reaction of sulfonyl halides with alcohols, for example with p-dimethylaminopyridine.

If a two-phase reaction is carried out it is useful to add a phase transfer catalyst, e.g. a quaternary ammonium or phosphonium salt, a polyalkylene ether or a crown ether.

As most benzoin sulfonates are crystalline compounds, they can be most simply isolated from the reaction mixture by direct crystallisation. The sulfonate often begins to crystallise from the reaction mixture by itself towards the end of the reaction.

The crystallisation can be accelerated by cooling the reaction mixture. The respective amount of solvent and the addition of water should be so chosen that, at the conclusion of the reaction, the base salt remains completely in solution, while the benzoin sulfonate should preferably crystallise out fully.

After the addition of base, the ratio of water to solvent is 1:100 to 10:1, preferably 1:25 to 1:1.

If the benzoin sulfonate is liquid, then it is best to carry out the reaction in a water-immiscible solvent. After the reaction, the aqueous layer is separated and the benzoin sulfonate is isolated by concentrating the organic phase. Before it is concentrated, the organic phase should first be washed until neutral and dried. Concentration of the organic phase should also be effected preferably at low temperature so as to avoid hydrolysis of the benzoin sulfonate.

Regardless of the solvent employed and the base, the reaction should be carried out at fairly low temperature, preferably in the range from 0° to 25° C., thereby making it necessary to cool the reaction medium.

A material advantage of carrying out the process of this invention in the presence of water instead of under anhydrous conditions is that it is not necessary to isolate solid bases or base salts and that therefore the sulfonic acid ester can be isolated direct from the reaction solution by crystallisation. A further advantage is that the solvent employed need not be free from water, so that drying the solvent and the reactor in a special step before the reaction can be dispensed with. The process affords the desired sulfonic acid esters in high yield and excellent purity.

The following Examples illustrate the invention in more detail, but imply no limitation to the procedures described therein.

EXAMPLE 1

Benzoin p-toluenesulfonate

With stirring, 424.5 g (2.0 moles) of benzoin are added to 650 ml of methyl ethyl ketone in a 2.5 liter sulfonating flask. The resultant beige suspension is stirred for 5 minutes, then 400.4 g (2.1 moles) of pulverised p-toluenesulfonyl chloride are added. No chemical reaction takes place as yet. The temperature falls from room temperature to c. +5° C. When the addition is complete, the suspension is stirred for a further 5 minutes and then 50 ml of deionised water are added. Then 293.3 g of 30% aqueous sodium hydroxide solution (corresponding to 2.2 moles of NaOH) are added dropwise over 30 minutes, while keeping the temperature at 10°-15° C. by cooling with an ice bath. The beige suspension is efficiently stirred at this temperature for 6 hours, then cooled to −10° to −15° C. and vigorously further stirred for a further hour at this temperature. The beige crystal slurry, which is readily stirrable up to the end, is isolated by filtration, washed with 1 to 3×200 ml of deionised water and thereafter once with 150 ml of aqueous ice-cold methyl ethyl ketone, and dried under vacuum at room temperature, to give 674 g (92% of theory) of benzoin p-toluenesulfonate in the form of white crystals which melt at 99°-101° C. The purity of the product is at least 98% according to analysis by thin-layer chromatography and NMR spectroscopy. A sample stirred in water shows no acid reaction to litmus paper.

Analysis: $C_{21}H_{18}O_4S$, theory: 68.83% C, 4.95% H, 8.75% S, found: 68.61% C, 4.98% H, 8.63% S.

In analogous manner it is possible to carry out the reaction in aqueous acetone. The procedure comprises reacting 0.1 mole of benzoin in 30 ml of acetone + 5 ml of water with 0.105 mole of p-toluenesulfonyl chloride and 0.11 mole of 30% aqueous NaOH for 7 hours at 10°-15° C., to give the sulfonate in 91% yield by direct crystallisation from the reaction solution.

EXAMPLE 2

Benzoin p-bromobenzenesulfonate

In accordance with the procedure described in Example 1, 0.2 mole of benzoin in 65 ml of methyl ethyl ketone and 5 ml of water are reacted with 0.22 mole of p-bromobenzenesulfonyl chloride and 0.24 mole of 30% aqueous NaOH at 10°-15° C. The reaction mixture is filtered and the filter product is washed with water and cold methyl ethyl ketone and dried under vacuum, to give the desired sulfonate with a melting point of 114°-122° C.

The analogous reaction of 0.1 mole of benzoin with 0.105 mole of p-bromobenzenesulfonyl chloride in 30 ml of tetrahydrofuran and 5 ml of water with the addition of 0.11 mole of 30% NaOH yields the same compound.

EXAMPLE 3

Benzoin m-nitrobenzenesulfonate

In accordance with the procedure of Example 2, 3-nitrobenzenesulfonyl chloride is reacted with benzoin in methyl ethyl ketone and aqueous NaOH. The resultant sulfonate melts at 92°-96° C.

EXAMPLE 4

4,4'-Dichlorobenzoin toluenesulfonate

In accordance with Example 2, p-toluenesulfonyl chloride is reacted with 4,4'-dichlorobenzoin in 200 ml of methyl ethyl ketone. The resultant sulfone melts at 129°-130° C.

EXAMPLE 5

4,4'-Dimethylbenzoin toluenesulfonate

In accordance with the procedure of Example 4, the sulfonate obtained melts at 94°-95° C.

EXAMPLE 6

Benzoin β-naphthylsulfonate 0.1 mole of benzoin and 0.12 mole of β-naphthalenesulfonyl chloride are dissolved at room temperature in 500 ml of tetrahydrofuran. After addition of 0.15 mole of 30% sodium hydroxide solution the mixture is stirred for 8 hours at room temperature. The reaction solution is diluted with 200 ml of methylene chloride and the organic phase is washed once with NaHCO$_3$ solution and once with water. The organic solution is dried over MgSO$_4$, dried and concentrated by evaporation. The residue is crystallised from hexane/ethyl acetate. The resultant sulfonate melts at 107°-109° C.

EXAMPLE 7

Benzoin benzenesulfonate

In accordance with Example 6, the sulfonate is obtained from benzoin and benzenesulfonyl chloride. Melting point: 89°-90° C.

What is claimed is:

1. In the process for the preparation of a sulfonic acid ester of formula I

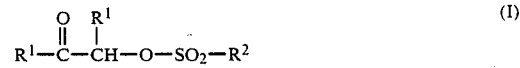

wherein
R$^1$ is phenyl or phenyl which is substituted by halogen, C$_1$-C$_4$alkyl, C$_1$-C$_4$alkoxy, C$_1$-C$_4$alkylthio, —NH—CO—(C$_1$-C$_4$alkyl), —NH—CO—phenyl, morpholino, piperidino or a radical —N(R$^3$)(R$^4$), or is naphthyl or tetrahydronaphthyl, each unsubstituted or substituted by halogen or C$_1$-C$_6$alkyl, or is a univalent 5- or 6-membered heteroaromatic radical which contains O, S or N and is unsubstituted or substituted by halogen or C$_1$-C$_4$alkyl, R$^2$ is phenyl or phenyl which is substituted by halogen, C$_1$-C$_{20}$alkyl, C$_1$-C$_4$haloalkyl, C$_1$-C$_4$alkoxy, C$_1$-C$_4$alkylthio, nitro, —NH—CO—(C$_1$-C$_4$-alkyl), —NH—CO—phenyl or benzoyl, or is naphthyl or naphthyl which is substituted by halogen or C$_1$-C$_{20}$ alkyl, or is a univalent 5- or 6-membered heteroaromatic radical which contains O, S or N and is unsubstituted or substituted by halogen or C$_1$-C$_6$alkyl, and R$^3$ and R$^4$ are each independently of the other C$_1$-C$_4$alkyl, allyl, or cyclohexyl, by reaction of a benzoin compound of formula II

with a sulfonyl halide of formula III

wherein X is fluorine, chlorine, bromine, in an inert organic solvent, the improvement comprising conducting said reaction in the presence of an aqueous solution of NaOH or KOH with a NaOH/KOH to sulfonyl halide mole ratio of 1:1 to 1.5:1 and at a reaction temperature below 40° C.

2. A process according to claim 1, which comprises the use of a compound of formula II, wherein R$^1$ is phenyl or phenyl which is substituted by halogen, C$_1$-C$_4$alkyl, C$_1$-C$_4$alkoxy or C$_1$-C$_4$alkylthio, or naphthyl, furyl, pyridyl or thienyl, each unsubstituted or substituted by C$_1$-C$_6$alkyl.

3. A process according to claim 1, which comprises the use of a compound of formula II, wherein R$^1$ is phenyl, chlorophenyl or tolyl.

4. A process according to claim 1, which comprises the use of a compound of formula III, wherein X is chlorine.

5. A process according to claim 1, which comprises the use of a compound of formula III, wherein R$^2$ is phenyl, naphthyl or pyridyl, each unsubstituted or substituted by halogen, C$_1$-C$_{20}$alkyl, halomethyl, C$_1$-C$_4$alkoxy, nitro or —NH—CO—C$_1$-C$_4$alkyl.

6. A process according to claim 1, which comprises the use of a compound of formula III, wherein R$^2$ is phenyl, bromophenyl, nitrophenyl, tolyl or naphthyl.

7. A process according to claim 1, wherein the reaction is carried out in the temperature range from 0° to 25° C.

8. A process according to claim 1, wherein the solvent is methyl ethyl ketone, toluene, xylene, methylene chloride, chlorobenzene, dichlorobenzene, dibutyl ether, methyl isobutyl ketone, acetone, dioxane, tetrahydrofuran or dimethylformamide.

9. A process according to claim 1, wherein the solvent is methyl ethyl ketone, acetone or tetrahydrofuran.

* * * * *